United States Patent
Kim et al.

(10) Patent No.: US 11,320,530 B2
(45) Date of Patent: May 3, 2022

(54) METHOD AND APPARATUS FOR REMOVING MOTION ARTIFACT OF UNFIXED RADAR

(71) Applicant: ELECTRONICS AND TELECOMMUNICATIONS RESEARCH INSTITUTE, Daejeon (KR)

(72) Inventors: Dong Kyoo Kim, Daejeon (KR); You Jin Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 212 days.

(21) Appl. No.: 16/690,867

(22) Filed: Nov. 21, 2019

(65) Prior Publication Data

US 2020/0166627 A1    May 28, 2020

(30) Foreign Application Priority Data

Nov. 26, 2018  (KR) .......................... 10-2018-0147845
Nov. 13, 2019  (KR) .......................... 10-2019-0144711

(51) Int. Cl.
   *G01S 13/524*   (2006.01)

(52) U.S. Cl.
   CPC ................ *G01S 13/5242* (2013.01)

(58) Field of Classification Search
   CPC ..... A61B 5/024; A61B 5/0507; A61B 5/0816; A61B 5/7207; G01S 13/5242; G01S 13/86; G01S 13/88
   See application file for complete search history.

(56) References Cited

U.S. PATENT DOCUMENTS

| | | | |
|---|---|---|---|
| 8,754,806 B2 | 6/2014 | Park et al. | |
| 9,791,561 B2 | 10/2017 | Rhee et al. | |
| 2006/0176214 A1* | 8/2006 | Nakagawa | G01S 7/4026 342/174 |
| 2015/0196213 A1* | 7/2015 | Pandia | A61B 5/725 600/509 |
| 2015/0289818 A1* | 10/2015 | LeBoeuf | A61B 5/0022 600/473 |
| 2015/0342467 A1* | 12/2015 | LeBoeuf | A61B 5/6816 600/476 |
| 2016/0209260 A1 | 7/2016 | Rice et al. | |

(Continued)

FOREIGN PATENT DOCUMENTS

| | | |
|---|---|---|
| KR | 1020180095340 A | 8/2018 |
| WO | 2007136610 A3 | 6/2008 |
| WO | 2017097907 A1 | 6/2017 |

*Primary Examiner* — Timothy X Pham
(74) *Attorney, Agent, or Firm* — Rabin & Berdo, P.C.

(57) ABSTRACT

A method and an apparatus for removing a motion artifact of a radar are provided. The method includes: obtaining a radar signal for a target to be measured by the radar; measuring posture of the radar; estimating a motion artifact caused by movement of the radar based on a vertical angle, a horizontal angle based on the posture of the radar, and displacement; and correcting the radar signal according to the motion artifact. The posture of the radar includes the vertical angle at which the radar signal is radiated in a vertical direction about a central axis, the horizontal angle at which the radar signal is radiated in a horizontal direction about the central axis, and the displacement of the radar according to the movement of the radar.

19 Claims, 11 Drawing Sheets

(56) References Cited

U.S. PATENT DOCUMENTS

| | | |
|---|---|---|
| 2016/0228010 A1 | 8/2016 | Kim et al. |
| 2017/0296093 A1 | 10/2017 | Ravid et al. |
| 2018/0294564 A1 | 10/2018 | Kim |
| 2019/0216341 A1* | 7/2019 | Bae .................... A61B 5/14553 |
| 2019/0219673 A1* | 7/2019 | Morinaga ................. G01S 7/40 |
| 2019/0286233 A1* | 9/2019 | Newberry ............... G06F 1/169 |

* cited by examiner

FIG. 2
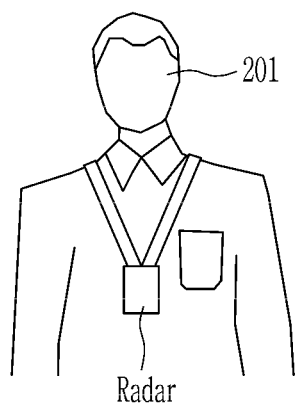
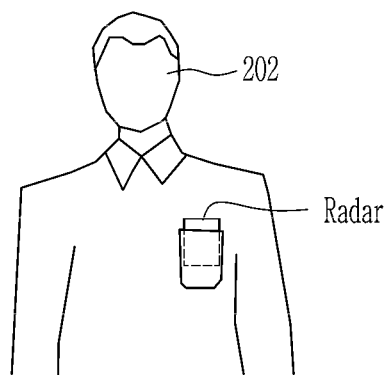
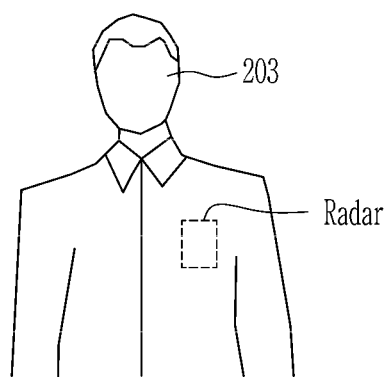

METHOD AND APPARATUS FOR REMOVING MOTION ARTIFACT OF UNFIXED RADAR

CROSS-REFERENCE TO RELATED APPLICATION

This application claims priority to and the benefit of Korean Patent Application Nos. 10-2018-0147845 filed in the Korean Intellectual Property Office on Nov. 26, 2018 and 10-2019-0144711 filed in the Korean Intellectual Property Office on Nov. 13, 2019, the entire contents of which are incorporated herein by reference.

BACKGROUND OF THE INVENTION

(a) Field of the Invention

The present invention relates to an unfixed radar, and more particularly, to a method and apparatus for removing motion artifacts of an unfixed radar.

(b) Description of the Related Art

Radar technology has traditionally been used in defense, aviation, and shipping, and its applications are currently expanding to security, location recognition, bio-signal recognition, and the like through a variety of studies. Among them, the bio-signal recognition field can be widely applied to where bio-signals of the human body can be utilized in medical, biomedical, and security. As the demand for technical solutions for various methods of bio-signal sensing has increased, the bio-signal recognition field has been receiving much attention recently. In this regard, recently, interest in technology for measuring respiration or heartbeat of the human body with a non-invasive and non-contact manner is increasing.

Conventional methods of measuring respiration or heartbeat are limited to contact devices with inconveniences that they need to be attached directly to the body, such as an electrocardiogram device, an optical-based pulse measuring device, or a belt-worn respiration measuring device. In order to alleviate these inconveniences, a method using an image in which the measuring device does not directly touch the body has been recently studied. This method estimates heartbeat by detecting tiny skin color changes caused by blood through facial images of the human body. While this method alleviates contact inconvenience, it is difficult to obtain constant sensing performance depending on the ambient light level.

A method of measuring bio-signals using radar has been studied. This method enables the detection of chest movements caused by heartbeat and respiration from a long distance with the use of radar, and is emerging in the field of bio-signal sensing because it is not affected by external lighting or weather.

The method of measuring bio-signals using radar is largely classified into a pulse radar method and a Doppler radar method. The pulse radar method estimates the motion of a human body by measuring the arrival time of a pulse through transmitting and receiving the pulse. This method is generally easy to measure the pattern of bulk motion (which represents large motion and includes, for example, walking, running, swinging arms in place, and the like). In addition, the pulse radar method is capable of measuring respiration, has been applied to the field of measuring sleep patterns using the results of the respiration measurement, and has recently been developed to be commercialized in the field of bio-signal sensing.

The Doppler radar method estimates the motion of the human body by measuring the arrival phase difference of a carrier by transmitting and receiving the carrier. Unlike the method of transmitting/receiving a pulse, it is possible to measure microscopic motions such as heartbeat and bulk motions depending on the value of the carrier frequency, and research is being actively conducted on bio-signal measurement radar technology that will emerge in the future.

However, when measuring heartbeat and respiration with a pulse radar or a Doppler radar in the prior art, both radar and human body movements should be limited. Accordingly, the measurement is not easy, and the application range of the radar is limited, thereby reducing practical use.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a method and an apparatus for removing motion artifacts caused by a movement of radar in an unfixed radar.

An exemplary embodiment of the present invention provides a method for removing a motion artifact of a radar. The method includes: obtaining, by an apparatus, a radar signal for a target to be measured by the radar; measuring, by the apparatus, posture of the radar wherein the posture of the radar includes a vertical angle at which the radar signal is radiated in a vertical direction about a central axis, a horizontal angle at which the radar signal is radiated in a horizontal direction about the central axis, and displacement of the radar according to movement of the radar; estimating, by the apparatus, a motion artifact caused by the movement of the radar based on the vertical angle, the horizontal angle, and the displacement; and correcting, by the apparatus, the radar signal according to the motion artifact.

In an embodiment, the radar signal may be a phase signal corresponding to a phase difference between a transmission signal and a reception signal when the radar is a Doppler radar and the radar signal may be a received pulse arrival time when the radar is a pulse radar.

In an embodiment, the estimating a motion artifact may include obtaining an amount of change in a distance between a surface of the target to be measured and the radar, and the correcting the radar signal may include using the amount of change in the distance as the motion artifact and correcting the radar signal according to the amount of change in distance.

In an embodiment, the correcting the radar signal may include subtracting a value corresponding to the amount of change in the distance from the radar signal to obtain a radar signal from which the motion artifact is removed.

In an embodiment, the obtaining an amount of change in a distance may include calculating the amount of change in the distance based on the radar signal, the vertical angle, and the displacement.

In an embodiment, if the radar is the Doppler radar, the amount of change in the distance may be calculated according to the following equation:

$$\Delta \hat{d}(n) = (1 - \cos\theta(n))\left(\frac{\lambda}{4\pi}\phi_{filt}(n) + l(n)\right),$$

wherein $\Delta \hat{d}(n)$ represents the amount of change in the distance, $\theta(n)$ represents the vertical angle, $l(n)$ represents the displacement, and $\phi_{filt}(n)$ represents the radar signal that is the phase signal or the filtered radar signal.

In an embodiment, if the radar is the pulse radar, the amount of change in the distance may be calculated according to the following equation:

$$\Delta \hat{d}(n) = (1-\cos\theta(n))(c \cdot p_{filt}(n)+l(n)),$$

wherein $\Delta \hat{d}(n)$ represents the amount of change in the distance, $\theta(n)$ represents the vertical angle, $l(n)$ represents the displacement, $p_{filt}(n)$ represents the radar signal that is is the received pulse arrival time or the filtered radar signal, and $c=3\times10^8$ (m/s).

In an embodiment, the obtaining an amount of change in a distance may include: obtaining a rotation angle when the radar rotates with the vertical angle and the horizontal angle; and calculating the amount of change in the distance based on the radar signal, the rotation angle, and the displacement.

In an embodiment, if the radar is the Doppler radar, the amount of change in the distance may be calculated according to the following equation:

$$\Delta \hat{d}(n) = (1 - \cos\beta(n))\left(\frac{\lambda}{4\pi}\phi_{filt}(n) + l(n)\right),$$

wherein $\Delta \hat{d}(n)$ represents the amount of change in the distance, $\beta(n)$ represents the rotation angle, $l(n)$ represents the displacement, and $\phi_{filt}(n)$ represents the radar signal that is the phase signal or the filtered radar signal.

In an embodiment, if the radar is the pulse radar, the amount of change in the distance may be calculated according to the following equation:

$$\Delta \hat{d}(n) = (1-\cos\beta(n))(c \cdot p_{filt}(n)+l(n)),$$

wherein $\Delta \hat{d}(n)$ represents the amount of change in the distance, $\beta(n)$ represents the rotation angle, $l(n)$ represents the displacement, $p_{filt}(n)$ represents the radar signal that is is the received pulse arrival time or the filtered radar signal, and $c=3\times10^8$ (m/s).

In an embodiment, the method may further include, after obtaining the radar signal, filtering the radar signal according to a preset band, and the estimating a motion artifact may include estimating a motion artifact using the filtered radar signal.

In an embodiment, the radar may be an unfixed radar.

In an embodiment, the target may be a human body, and the radar signal may be a signal corresponding to a heartbeat and respiration of the human body.

Another embodiment of the present invention provides an apparatus for removing a motion artifact of a radar. The apparatus includes: a filtering unit configured to obtain and filter a radar signal for a target to be measured by the radar; a radar detection unit configured to measure posture of the radar wherein the posture of the radar includes a vertical angle at which the radar signal is radiated in a vertical direction about a central axis, a horizontal angle at which the radar signal is radiated in a horizontal direction about the central axis, and displacement of the radar according to movement of the radar; and a radar posture correction unit configured to estimate a motion artifact caused by the movement of the radar based on the vertical angle, the horizontal angle, and the displacement which are provided from the radar detection unit and correct the radar signal provided from the filtering unit according to the motion artifact.

In an embodiment, the radar posture correction unit may be configured to obtain an amount of change in a distance between a surface of the target to be measured and the radar, use the amount of change in the distance as the motion artifact, and correct the radar signal according to the amount of change in distance.

In an embodiment, the radar posture correction unit may be configured to subtract a value corresponding to the amount of change in the distance from the radar signal to obtain a radar signal from which the motion artifact is removed.

In an embodiment, the radar posture correction unit may be configured to calculate the amount of change in the distance based on the radar signal, the vertical angle, and the displacement.

In an embodiment, the radar posture correction unit may be configured to obtain a rotation angle when the radar rotates with the vertical angle and the horizontal angle and calculates the amount of change in the distance based on the radar signal, the rotation angle, and the displacement.

In an embodiment, the radar signal may be a phase signal corresponding to a phase difference between a transmission signal and a reception signal when the radar is a Doppler radar, and the radar signal may be a received pulse arrival time when the radar is a pulse radar.

In an embodiment, the radar may be unfixed, the target may be a human body, and the radar signal may be a signal corresponding to a heartbeat and respiration of the human body.

BRIEF DESCRIPTION OF THE DRAWINGS

FIG. 2 is an exemplary diagram illustrating a state of measuring a bio-signal using radar according to an exemplary embodiment of the present invention.

DETAILED DESCRIPTION OF THE EMBODIMENTS

Figure 1:
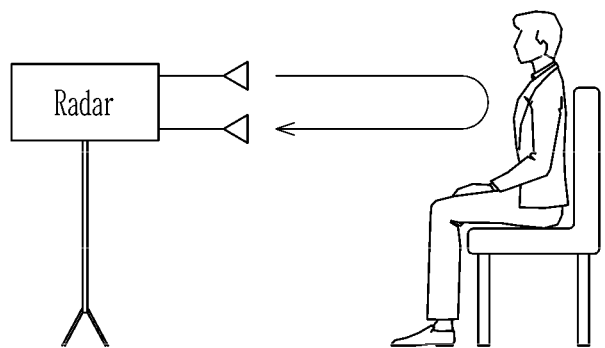
FIG. 1 is a diagram illustrating a bio-signal measuring method using conventional radar.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, in addition, unless explicitly described to the contrary, the word "comprise" and variations such as "comprises" or "comprising" will be understood to imply the inclusion of stated elements but not the exclusion of any other elements.

The expressions described in the singular may be interpreted as singular or plural unless an explicit expression such as "one", "single", and the like is used.

In addition, terms including ordinal numbers such as "first" and "second" used in embodiments of the present disclosure may be used to describe components, but the components should not be limited by the terms. The terms are only used to distinguish one component from another. For example, without departing from the scope of the present disclosure, a first component may be referred to as a second component, and similarly, the second component may be referred to as the first component. In addition, terms including ordinal numbers such as first and second used in embodiments of the present invention may be used to describe components, but the components should not be limited by the terms.

Hereinafter, a method and apparatus for removing motion artifacts of an unfixed radar according to an embodiment of the present invention will be described.

FIG. 1 is a diagram illustrating a bio-signal measuring method using a conventional radar.

When heartbeat and respiration are measured by a pulse radar or a Doppler radar, the radar is positioned outside a certain distance from the human body, as shown in FIG. 1. A measurement is then made, in which the human body must maintain a posture with minimal movement or a stationary posture, i.e. sitting or lying down. The reason for minimizing the movement of the human body at the time of measurement is that it is very difficult to extract signals corresponding to heartbeat and respiration when human movements other than heartbeat and respiration are detected in radar signals, since the movement of the signal corresponding to the heartbeat and respiration of the human body to be measured is very small (generally, the chest movement due to the heartbeat and respiration is 1 mm or less and several mm, respectively).

When measuring the bio-signal using the existing radar, both the radar and the human body movements must be limited, so the range in which radars are used is limited and their use in real life is diminished.

In an embodiment of the present invention, the heartbeat and respiration are measured while a radar is in close proximity to the human body.

FIG. 2 is an exemplary diagram illustrating a state of measuring a bio-signal using a radar according to an exemplary embodiment of the present invention.

In an exemplary embodiment of the present invention, as shown in FIG. 2, the bio-signal is measured in a state in which the radar is in close proximity to the human body. This proximity measurement includes a measurement scenario when the radar is worn on the body. For example, a state in which a radar is worn in the form of a necklace 201, a state in which a radar is placed in a pocket of a garment 202, and a state 203 in which a radar is embedded in a garment may be considered.

In the measurement scenario in which the radar is worn on the body, the radar is positioned at a close proximity to the human body.

Figure 3:
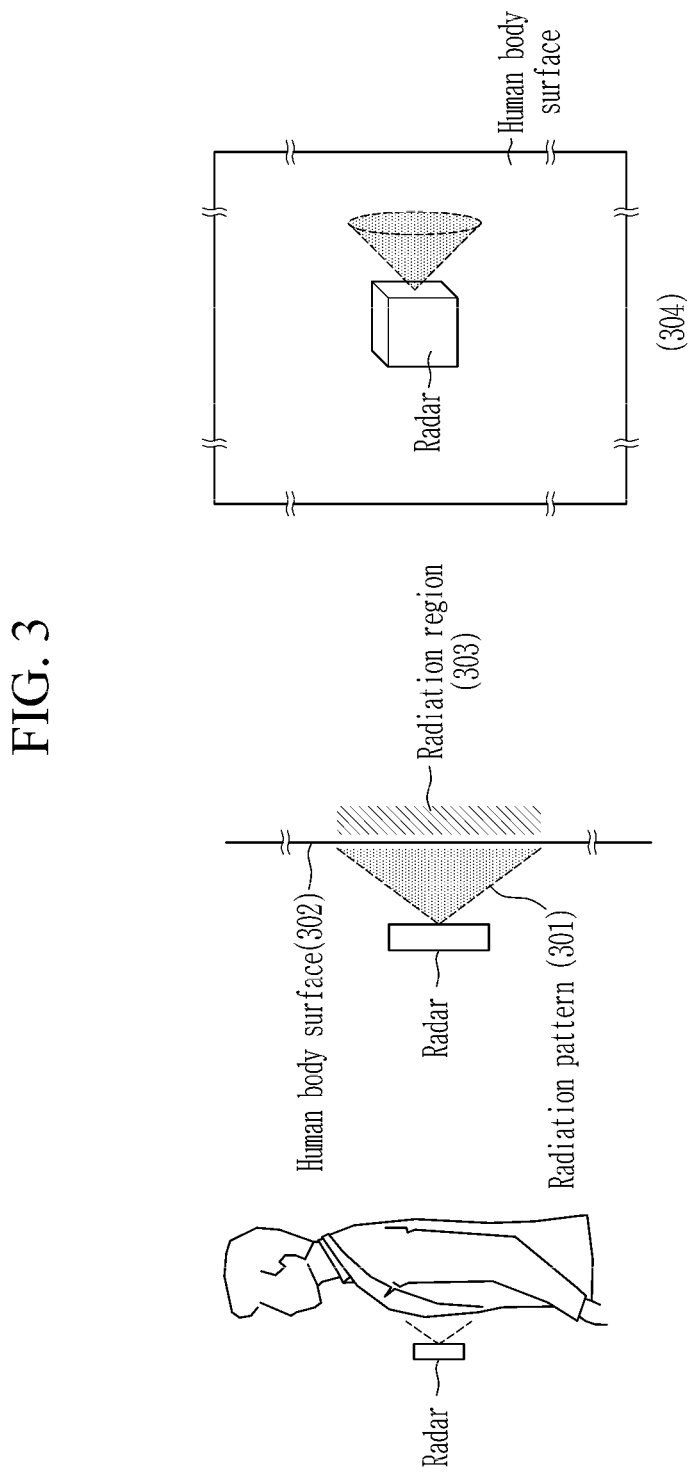
FIG. 3 is an exemplary diagram illustrating a human body area according to a detection area of a radar when measuring a bio-signal using the radar according to an exemplary embodiment of the present invention.

FIG. 3 is an exemplary diagram illustrating a human body area according to a detection area of a radar when measuring a bio-signal using radar according to an exemplary embodiment of the present invention.

When the radar is close to the human body (for example, when the distance between the radar and the human body is within a few cm), the detection area of the radar is narrowed so that the area of the human body is much larger than that of the detection area of the radar.

Specifically, when the measurement is performed in a state in which the radar is in close proximity to the human body, a radiation pattern 301 of the radar is radiated onto a surface 302 of the human body to form a radiation region 303, that is, the detection region. However, since the distance between the radar and the human body is very small, the detection area of the radar is significantly smaller than a human body area 304. That is, as the area of the human body is very large compared to the detection area of the radar, a relationship between the radar and the human body surface can be assumed.

Considering the above assumptions, in the embodiment of the present invention, the heartbeat and respiration of the human body are measured without fixing the radar, unlike the prior art.

Hereinafter, the signals corresponding to the heartbeat and respiration of the human body are referred to as "a heartbeat and respiration signal".

Figure 4:
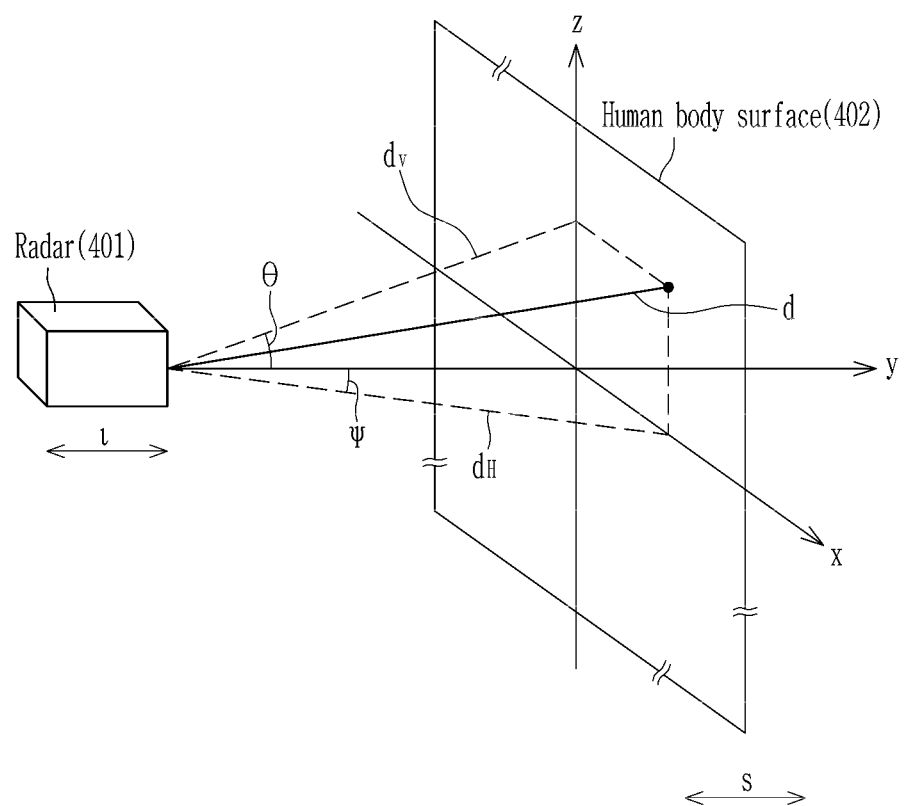
FIG. 4 is a diagram illustrating a relationship between the radar and the human body surface according to an embodiment of the present invention.

In order to define the movement of the unfixed radar, the radar and the human body surface are defined as shown in FIG. 4 in the embodiment of the present invention.

FIG. 4 is a diagram illustrating a relationship between the radar and the human body surface according to an embodiment of the present invention.

The distance between a radar 401 and a human body surface 402 is defined as d, and the movement of the radar is represented by a vertical angle $\theta$, a horizontal angle $\psi$, and a displacement I. Specifically, the movement of the radar includes a vertical angle $\theta$ and a horizontal angle $\psi$ at which a signal is radiated from the radar, and includes a displacement I of the radar according to the movement of the radar itself. The movement of the human heartbeat and respiration signal is represented by the movement s of the human body surface 402.

Since the radar is unfixed, errors can occur in the signal measured by the radar as the radar moves. Therefore, in the embodiment of the present invention, the movement of the radar according to the vertical angle $\theta$, the horizontal angle $\psi$, and the displacement I is removed from the signal measured by the radar. This will be described in more detail later.

Figure 5:
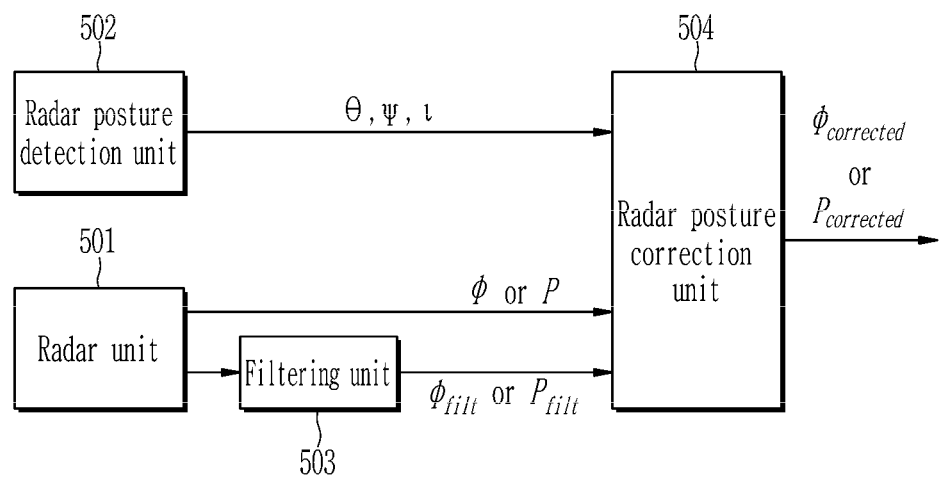
FIG. 5 is a diagram illustrating a structure of a radar system according to an embodiment of the present invention.

FIG. 5 is a diagram illustrating the structure of a radar system according to an embodiment of the present invention.

The radar system 500 includes a radar unit 501, a radar posture detection unit 502, a filter unit 503, and a posture correction unit 504.

The radar unit 501 outputs a signal to a target, receives a signal reflected from the target, and outputs a radar signal corresponding to the received signal. The radar unit 501 may be formed of a Doppler radar or a pulse radar. The signal output by the radar unit 501 may correspond to a bio-signal of a human body, and may correspond to, for example, a heartbeat and a respiration signal.

When the Doppler radar is used, the radar signal that is the output of the radar unit 501 becomes a phase signal φ corresponding to the phase difference between a transmission signal and a reception signal. When the pulse radar is used, the radar signal that is the output of the radar unit 501 becomes an arrival time p of a received pulse.

The filter unit 503 filters the radar signal. In an embodiment of the present invention, the filter unit 503 is a filter excluding signals other than those corresponding to the frequency bands of the heartbeat and respiration (which will be referred to as a preset band signal, for convenience of description). The filter unit 503 filters signals other than the preset band signal from the radar signal and then outputs the filtered signals. The output of the filter unit 503 is represented by $\phi_{filt}$ when the Doppler radar is used, and is represented by $p_{filt}$ when the pulse radar is used.

The radar posture detection unit 502 detects the posture of the radar.

Figure 6:
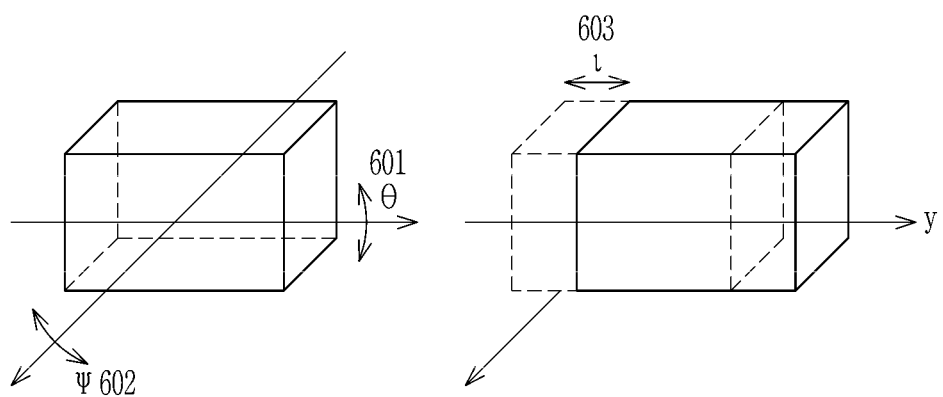
FIG. 6 is an exemplary diagram illustrating posture of a radar according to the embodiment of the present invention.

FIG. 6 is an exemplary diagram illustrating the posture of the radar according to the embodiment of the present invention.

The posture of the radar corresponds to the movement of the radar, and includes a vertical angle θ 601, a horizontal angle ψ 602, and displacement I 603, as shown in FIG. 6.

The vertical angle θ 601 represents the angle at which the signal from the radar unit 501 is radiated in the vertical direction about the central axis, the horizontal angle ψ 602 represents the angle at which the signal from the radar unit 501 is radiated in the horizontal direction about the central axis, and the displacement I 603 corresponds to the amount of movement according to the movement of the radar unit 501 itself on the axis (e.g. a y-axis) in the direction in which the radar signal is radiated.

The radar posture detection unit 502 detects the vertical angle θ 601, the horizontal angle 602, and the displacement I 603, respectively, and outputs a posture detection signal corresponding thereto. To this end, the radar posture detection unit 502 may use an inertial measurement unit (IMU) or a vertical/horizontal array antenna. Methods of measuring a vertical angle, a horizontal angle, and a displacement using this are well known, and thus detailed descriptions thereof are omitted herein.

Meanwhile, the radar posture correction unit 504 receives the output of the radar posture detecting unit 502 and the output of the filter unit 503, and outputs a result of correcting the radar posture from the output of the radar unit 500. In detail, the radar posture correction unit 504 may correct the filtered radar signal $\phi_{filt}$ or $p_{filt}$ output from the filter unit 503 according to the posture detecting signals θ, ψ, and I provided from the radar posture detecting unit 502 to output the corrected radar signal $\phi_{corrected}$ or $p_{corrected}$.

In the radar system having such a structure, the apparatus for removing a motion artifact of the unfixed radar according to the embodiment of the present invention may be implemented based on the radar posture detection unit 502, the filter unit 503, and the posture correction unit 504.

Figure 7:
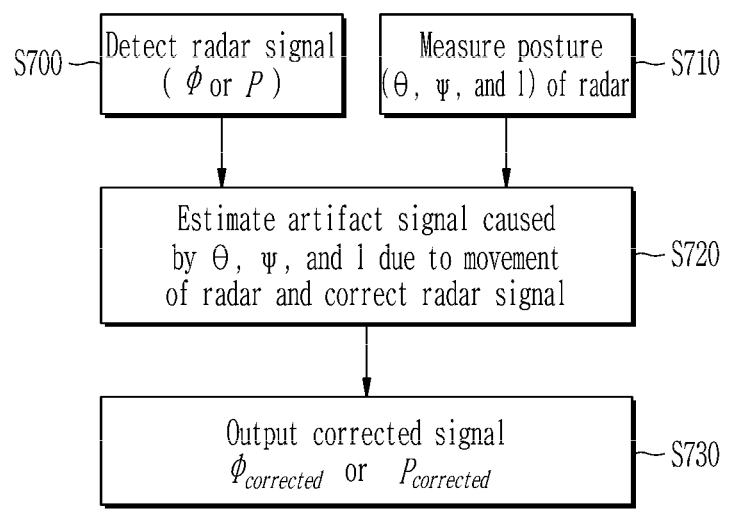
FIG. 7 is a flowchart illustrating a method for removing motion artifacts of an unfixed radar according to an embodiment of the present invention.

FIG. 7 is a flowchart illustrating a method for removing motion artifacts of unfixed radar according to an embodiment of the present invention.

As shown in FIG. 7, the radar unit of the radar system outputs the radar signal to the target, receives the signal reflected from the target, and outputs the radar signal corresponding to the received signal (S700).

On the other hand, the radar posture detection unit measures the vertical angle θ, the horizontal angle ψ, and the displacement I according to the movement of the radar (S710). Here, the order of performing steps S700 and S710 is not limited thereto. For example, after step S700 is performed, step S710 may be performed. Also, after step S710 may be performed, step S700 may then be performed.

The radar posture correction unit removes the movement due to the radar posture (θ, ψ, I) from the output (φ or p) of the radar. That is, an artifact signal due to the movement of the radar is estimated according to the posture detection signals θ, ψ, and I, and the radar signal is corrected based on the estimated artifact signal (S720). Here, the radar posture correction unit removes the movement due to the radar posture from the output ($\phi_{filt}$, $p_{filt}$) of the radar filtered by the filtering unit.

The radar signal correction process will now be described in detail.

First, for convenience of description, a method of removing a motion artifact by correcting a radar signal according to an embodiment of the present invention will be described based on the movement of the radar due to the vertical angle θ and the displacement I, excluding the horizontal angle ψ.

Figure 8:
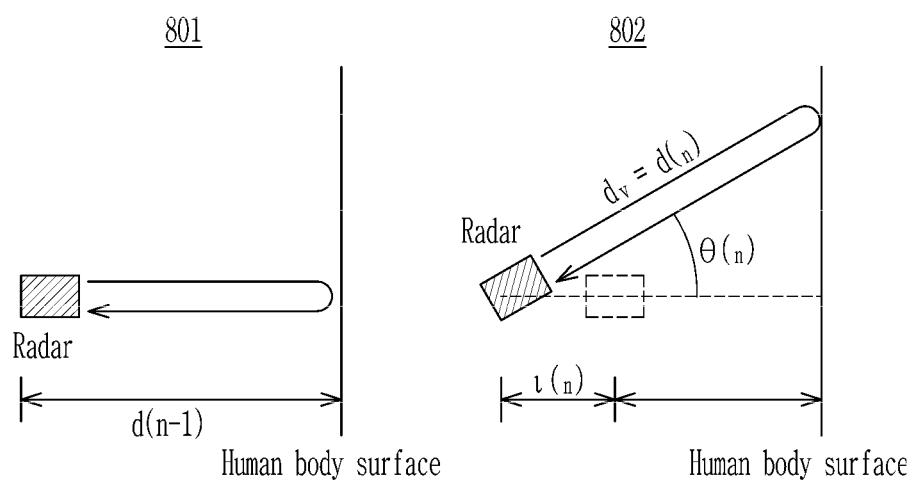
FIG. 8 is an exemplary diagram illustrating a vertical angle and displacement measurement according to the movement of the radar according to an embodiment of the present invention.

FIG. 8 is an exemplary diagram illustrating a vertical angle and displacement measurement according to the movement of the radar according to an embodiment of the present invention.

For example, the movement of the radar is measured at the first measurement time n−1 (801), and the movement of the radar is measured at the second measurement time n (802).

The vertical angle and displacement according to the movement of the radar measured at the first measurement time n−1 may be θ(n−1)=0 and l(n−1)=0, respectively. When the second measurement time n is reached from the first measurement time n−1, the distance change Δd(n)=d(n)−d(n−1) between the radar and the human body surface may be expressed as follows:

$$\Delta d(n) = \frac{1 - \cos\theta(n)}{\cos\theta(n)}(d(n-1) + l(n)) \quad \text{Equation 1}$$

wherein l(n) represents the displacement according to the movement of the radar measured at the second measurement time n.

When the radar is a Doppler radar, the radar signal that is the output of the radar unit is a phase signal φ. Using that the Doppler radar's received phase signal is $$\exp\left(j\frac{4\pi}{\lambda}x\right)$$

(here, x is a distance), and the phase signal φ can be expressed as follows.

$$\phi(n) = \operatorname{atan}(y(n)) = \frac{4\pi(d(n-1) + (1-\cos\theta(n)))}{\lambda\cos\theta(n)} \quad \text{Equation 2}$$

Through Equation 2, it can be seen that the radar signal ($\phi$ or p) has information $\theta(n)$ and a value l(n) about the movement of the radar. In the embodiment of the present invention, the signal generated due to the movement of the radar may be removed in consideration of this.

When the radar is the Doppler radar, the phase signal $\phi_{filt}(n)$ that is filtered by the filtering unit and the output signals $\theta(n)$ and l(n) of the radar posture detection unit are used.

After the measurement time reaches to n from n−1, the distance d(n) between the radar and the human body surface may be calculated as follows to estimate the amount of change in the distance between the radar and the human body surface as the radar posture changes.

$$\hat{d}(n) = \frac{\lambda}{4\pi}\phi_{filt}(n)\cdot\cos\theta(n) - (1-\cos\theta(n))l(n) \quad \text{Equation 3}$$

The amount of change in the distance $\Delta\hat{d}(n)$ between the radar and the human body surface is calculated using Equation 3, as shown in Equation 4 below.

$$\Delta\hat{d}(n) = (1-\cos\theta(n))\left(\frac{\lambda}{4\pi}\phi_{filt}(n) + l(n)\right) \quad \text{Equation 4}$$

By correcting the radar signal (phase signal) of the Doppler radar based on the amount of change in the distance $\Delta\hat{d}(n)$ between the radar and the human body surface calculated according to Equation 4, a corrected radar signal is obtained as shown in Equation 5 below.

$$\phi_{corrected}(n) = \phi(n) - \frac{4\pi}{\lambda}\Delta\hat{d}(n) \quad \text{Equation 5}$$

On the other hand, the radar signal correction method when the radar is a pulse radar may be performed in a similar manner to the radar signal correction method when the radar is the Doppler radar described above.

Unlike the Doppler radar, the radar signal, which is the output of the pulse radar, is the arrival time (received pulse arrival time) p of the signal reflected back to the human body surface. The distance d(n) between the radar and the human body surface at the measurement time n may be calculated as shown in Equation 6 below.

$$\hat{d}(n) = c\cdot p(n)\cdot\cos\theta(n) - (1-\cos\theta(n))l(n) \quad \text{Equation 6}$$

here $c = 3\times 10^8$ (m/s).

The amount of change in the distance $\Delta\hat{d}(n)$ between the radar and the human body surface is calculated using Equation 6, as shown in Equation 7 below.

$$\Delta\hat{d}(n) = (1-\cos\theta(n))(c\cdot p_{filt}(n) + l(n)) \quad \text{Equation 7}$$

wherein $p_{filt}(n)$ may represent the received pulse arrival time filtered by the filtering unit.

By correcting the radar signal (received pulse arrival time) of the pulse radar based on the amount of change in the distance $\Delta\hat{d}(n)$ between the radar and the human body surface calculated according to Equation 7, a corrected radar signal as shown in Equation 8 is obtained.

$$p_{corrected}(n) = p(n) - \Delta\hat{d}(n) \quad \text{Equation 8}$$

As described above, the distance $\hat{d}(n)$ between the radar and the human body surface is calculated using the output signals $\theta(n)$ and l(n) of the radar posture detection unit and the amount of change in the distance $\Delta\hat{d}(n)$ between the radar and the human body surface is calculated according to the calculated distance $\hat{d}(n)$, and the radar signal (received pulse arrival time) based on the distance change amount is corrected, thereby removing the motion artifact from the radar signal.

In the above-described method, a method of removing a motion artifact by correcting the radar signal according to an embodiment of the present invention is described based the horizontal angle $\psi$ according to the movement of the radar, which is excluded for convenience of description.

Figure 9:
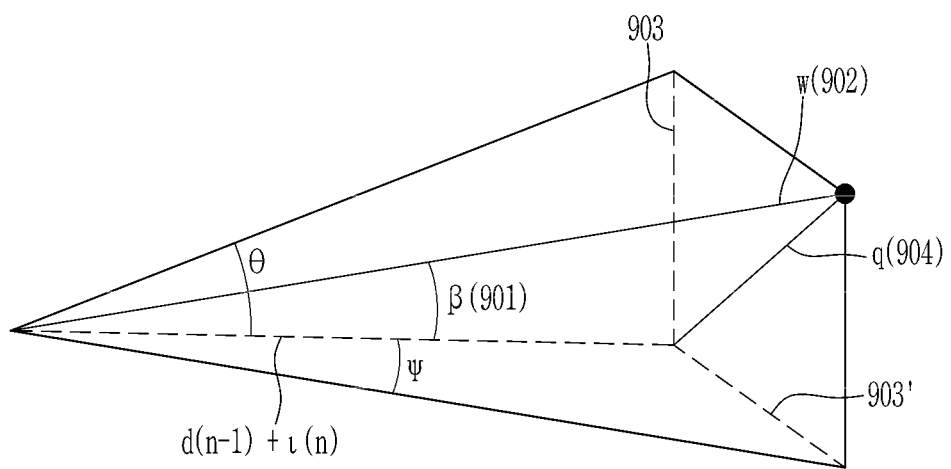
FIG. 9 is another exemplary diagram illustrating radar movement measurement according to an exemplary embodiment of the present invention.

FIG. 9 is another exemplary diagram illustrating radar motion measurement according to an exemplary embodiment of the present invention.

β 901 represents the rotation angle of the radar when the radar rotates with the vertical angle θ and the horizontal angle $\psi$. The cosine value of this rotation angle β is calculated. For this purpose, q (904) is first obtained. When the signal from the radar is radiated to the human body surface and the radiation area formed on the human body surface is rectangular, q 904 corresponds to the length of the diagonal of the rectangle.

A side 903 of the rectangle is $(d(n-1)+l(n))\cdot\tan\theta$, and the other side 903' is $(d(n-1)+l(n))\cdot\tan\psi$. Using this, q 904 can be expressed as Equation 9 below.

$$q = \sqrt{((d(n-1)+l(n))\cdot\tan\theta)^2 + ((d(n-1)+l(n))\cdot\tan\psi)^2} = \sqrt{(d(n-1)+l(n))^2(\tan^2\theta+\tan^2\psi)} \quad \text{Equation 9}$$

Meanwhile, w 902 may be calculated as follows using q 904 calculated based on Equation 9 above.

$$w = \sqrt{q^2 + (d(n-1)+l(n))^2} = (d(n-1)+l(n))\sqrt{\tan^2\theta+\tan^2\psi+1} \quad \text{Equation 10}$$

Therefore, since the cosine value of the rotation angle β is $$\cos\beta = \frac{(d(n-1)+l(n))}{w},$$

it can be simplified as a function of the vertical angle θ and the horizontal angle $\psi$ as shown in Equation 11 below.

$$\cos\beta = \frac{1}{\sqrt{\tan^2\theta+\tan^2\psi+1}} \quad \text{Equation 11}$$

Using Equation 11, the amount of change in the distance $\Delta\hat{d}(n)$ between the radar and the human body surface due to the rotation angle β and the displacement I of the radar can be obtained as follows.

$$\Delta\hat{d}(n) = (1-\cos\beta(n))\left(\frac{\lambda}{4\pi}\phi_{filt}(n) + l(n)\right) \quad \text{Equation 12}$$

When the radar is the Doppler radar, the amount of change in the distance $\Delta\hat{d}(n)$ between the radar and the human body surface due to the rotation angle β and the displacement I of the radar may be calculated according to Equation 12 based on Equation 4 above. In this case, the radar signal can be and corrected and obtained by applying the distance change amount $\Delta\hat{d}(n)$ calculated according to Equation 12 to Equation 5.

Meanwhile, when the radar is the pulse radar, the amount of change in the distance $\Delta\hat{d}(n)$ between the radar and the human body surface due to the rotation angle β and the displacement I of the radar may be calculated as in Equation 13 below.

$$\Delta\hat{d}(n) = (1 - \cos \beta(n))(c \cdot p_{fill}(n) + l(n))$$ Equation 13

The radar signal can be and corrected and obtained by applying the distance change $\Delta\hat{d}(n)$ calculated according to Equation 12 to Equation 8.

Through the process as described above, the artifact signal due to the movement of the radar (the amount of change in the distance between the radar and the human body surface, the amount of change in the distance between the radar and the human body surface due to the rotation angle β and the displacement I of the radar, and the like) is estimated from the output of the radar (Doppler radar or pulse radar), and the radar signal is corrected based on the estimated artifact signal.

Thereafter, the radar posture correction unit outputs the corrected radar signal ($\phi_{corrected}$ or $p_{corrected}$) as shown in FIG. 7 (S730).

Figure 10:
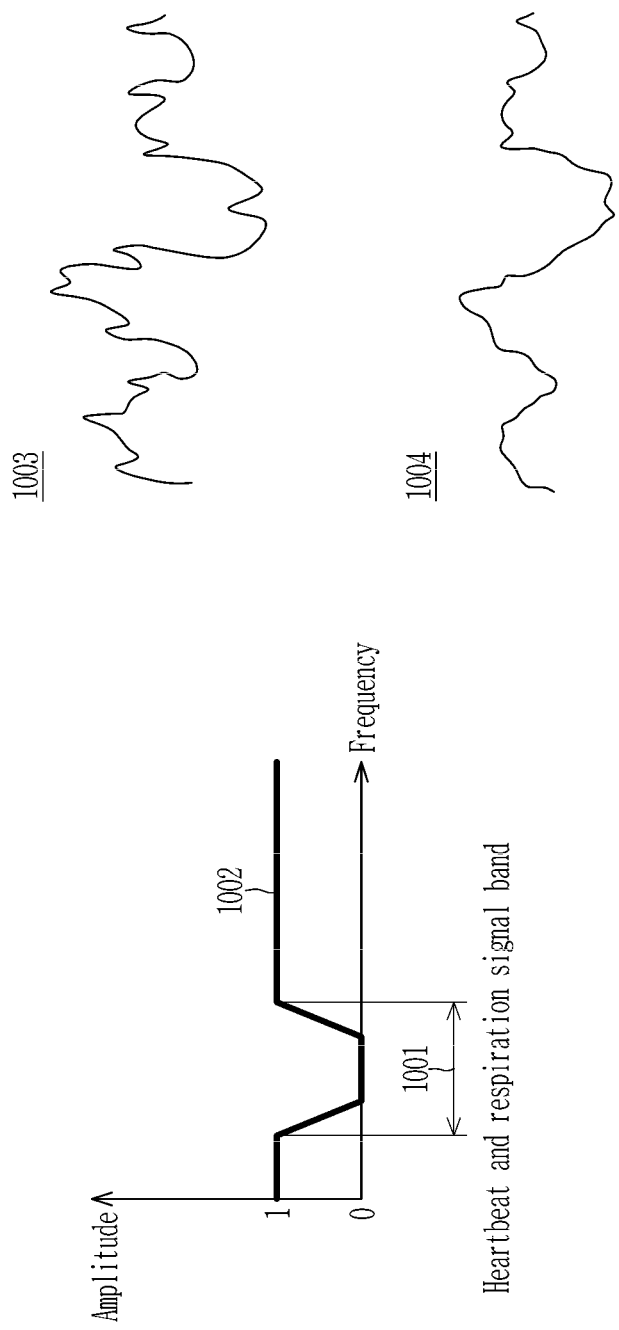
FIG. 10 is a diagram illustrating filter characteristics according to an exemplary embodiment of the present invention.

On the other hand, in the embodiment of the present invention, the filtering characteristics of the filter unit is as shown in FIG. 10.

FIG. 10 is a diagram illustrating filter characteristics according to an exemplary embodiment of the present invention.

As shown in FIG. 10, the filter unit has a characteristic 1002 of removing a frequency band 1001 of the heartbeat and respiration signal from the radar signal. For example, when a signal 1003 is input to the filter unit in FIG. 10, the output of the filter unit is a signal 1004 from which the heartbeat and respiration signal are removed. The filter unit helps the radar posture correction unit to estimate the distance change $\Delta\hat{d}(n)$ due to the radar posture, so that the radar posture correction unit can acquire a signal $p_{corrected}(n)$ with a more accurately corrected radar posture.

The method and apparatus according to the embodiment of the present invention allow easy implementation of a wearable radar. The wearable radar is not fixed, and is in a state where movement can occur and thus the quality of the radar signal deteriorates. However, according to the embodiment of the present invention, the motion artifact due to the movement of the radar is estimated and the radar signal is corrected based on the estimated artifact to obtain a more accurate radar signal. Therefore, the method and the apparatus according to the embodiment of the present invention can be used in a wearable radar for measuring a bio-signal such as heartbeat and respiration without fixing the radar, and as a result, can increase the practical use of the radar.

Figure 11:
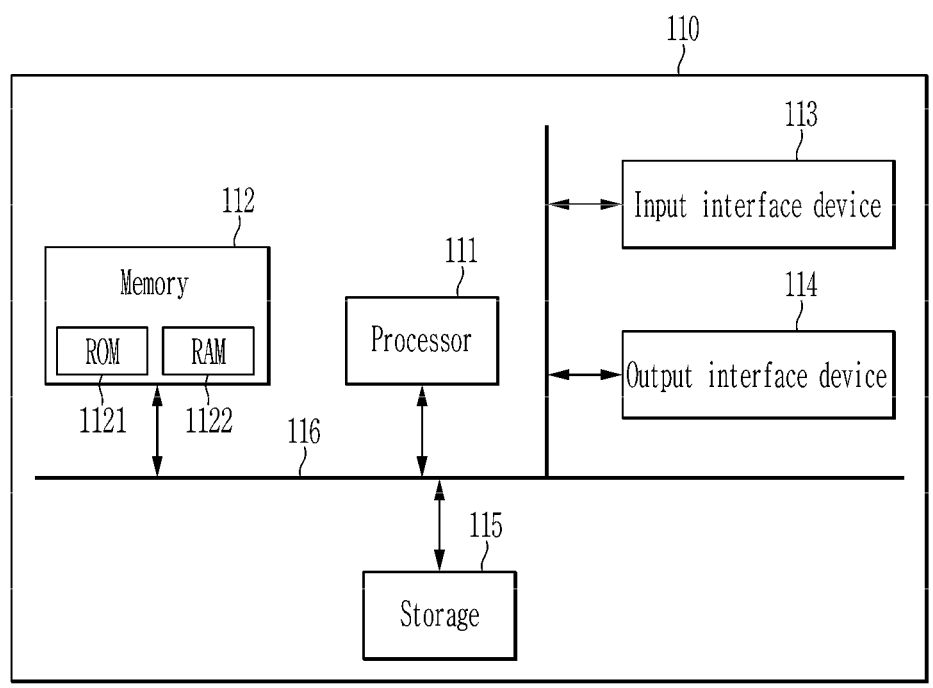
FIG. 11 is a structural diagram of an apparatus for motion artifacts according to another embodiment of the present invention.

FIG. 11 is a structural diagram of an apparatus for removing a motion artifact according to another embodiment of the present invention.

As shown in FIG. 11, the apparatus for removing motion artifact 110 according to the embodiment of the present invention includes a processor 111, a memory 112, an input interface device 113, an output interface device 114, and a storage 115, which can communicate via a bus 116.

The processor 111 may be configured to implement the methods described with reference to FIGS. 2 to 10 above.

For example, the processor 111 may be configured to perform the function of at least one of the radar posture detection unit, the filter unit, and the radar posture correction unit. The processor 111 may be a central processing unit (CPU) or a semiconductor device that executes instructions stored in the memory 112 or the storage 115.

The memory 112 is connected to the processor 111, and stores various information related to the operation of the processor 111. The memory 112 may store instructions for execution in the processor 111, or temporarily load the instructions from the storage 115. The processor 111 may execute instructions stored or loaded in the memory 112. The memory may include a ROM 1121 and a RAM 1122. In an embodiment of the present disclosure, the memory 112 and the storage 115 may be located inside or outside the processor 111, and may be connected to the processor 111 through various known means.

The input interface device 113 may be configured to receive input data and transfer the input data to the processor 111.

The output interface device 114 may be configured to output a processing result of the processor 111.

According to an exemplary embodiment of the present invention, an accurate radar signal may be obtained by effectively removing motion artifacts caused by the movement of the radar in the unfixed radar.

Therefore, the method and the apparatus according to the embodiment of the present invention can be easily applied to the field of measuring bio-signals. In this case, the heartbeat and respiration signal of the human body can be measured without fixing a radar, or the bio-signals can be measured using a radar without touching the human body while the subject is aware.

In addition, by effectively eliminating the motion artifacts generated by the movement of the radar in the unfixed radar, it can be used for wearable radar, which measures the heartbeat and respiration signals of the human body by wearing the radar on the body, and as a result, practical utilization of the radar can increase. In addition, it is possible to increase the compatibility of the radar by extending the application field of the biological radar.

An embodiment of the present invention is not implemented only through the above-described apparatus and/or method, but may be implemented through a program for realizing a function corresponding to the configuration of the embodiment of the present invention, a recording medium on which the program is recorded, and the like. Such implementations may be readily implemented by those skilled in the art from the description of the above-described embodiments.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A method for removing a motion artifact of a radar, comprising:
   obtaining, by an apparatus, a radar signal for a target to be measured by the radar;
   measuring, by the apparatus, posture of the radar wherein the posture of the radar includes a vertical angle at which the radar signal is radiated in a vertical direction about a central axis, a horizontal angle at which the radar signal is radiated in a horizontal direction about the central axis, and displacement of the radar which corresponds to an amount of movement according to movement of the radar itself on an axis in a direction in which the radar signal is radiated;

estimating, by the apparatus, a motion artifact caused by the movement of the radar based on the vertical angle, the horizontal angle, and the displacement; and correcting, by the apparatus, the radar signal according to the motion artifact.

2. The method of claim 1, wherein
the radar signal is a phase signal corresponding to a phase difference between a transmission signal and a reception signal when the radar is a Doppler radar and the radar signal is a received pulse arrival time when the radar is a pulse radar.

3. The method of claim 1, wherein
the radar is an unfixed radar.

4. A method for removing a motion artifact of a radar, comprising:

obtaining, by an apparatus, a radar signal for a target to be measured by the radar;

measuring, by the apparatus, posture of the radar wherein the posture of the radar includes a vertical angle at which the radar signal is radiated in a vertical direction about a central axis, a horizontal angle at which the radar signal is radiated in a horizontal direction about the central axis, and displacement of the radar according to movement of the radar;

estimating, by the apparatus, a motion artifact caused by the movement of the radar based on the vertical angle, the horizontal angle, and the displacement; and correcting, by the apparatus, the radar signal according to the motion artifact, wherein the estimating a motion artifact comprises:

obtaining an amount of change in a distance between a surface of the target to be measured and the radar, and the correcting the radar signal comprises using the amount of change in the distance as the motion artifact and correcting the radar signal according to the amount of change in distance.

5. The method of claim 4, wherein
the correcting the radar signal comprises
subtracting a value corresponding to the amount of change in the distance from the radar signal to obtain a radar signal from which the motion artifact is removed.

6. The method of claim 4, wherein
the obtaining an amount of change in a distance comprises
calculating the amount of change in the distance based on the radar signal, the vertical angle, and the displacement.

7. The method of claim 6, wherein
if the radar is a Doppler radar, the amount of change in the distance is calculated according to the following equation:

$$\Delta \hat{d}(n) = (1 - \cos\theta(n))\left(\frac{\lambda}{4\pi}\phi_{filt}(n) + l(n)\right),$$

wherein $\Delta \hat{d}(n)$ represents the amount of change in the distance, $\theta(n)$ represents the vertical angle, $l(n)$ represents the displacement, and $\phi_{filt}(n)$ represents the radar signal that is a phase signal or a filtered radar signal.

8. The method of claim 6, wherein
if the radar is a pulse radar, the amount of change in the distance is calculated according to the following equation:

$$\Delta\hat{d}(n) = (1 - \cos\theta(n))(c \cdot p_{filt}(n) + l(n)),$$

wherein $\Delta\hat{d}(n)$ represents the amount of change in the distance, $\theta(n)$ represents the vertical angle, $l(n)$ represents the displacement, $p_{filt}(n)$ represents the radar signal that is a received pulse arrival time or a filtered radar signal, and $c=3\times10^8$ (m/s).

9. The method of claim 4, wherein
the obtaining an amount of change in a distance comprises:

obtaining a rotation angle when the radar rotates with the vertical angle and the horizontal angle; and calculating the amount of change in the distance based on the radar signal, the rotation angle, and the displacement.

10. The method of claim 9, wherein
if the radar is a Doppler radar, the amount of change in the distance is calculated according to the following equation:

$$\Delta \hat{d}(n) = (1 - \cos\beta(n))\left(\frac{\lambda}{4\pi}\phi_{filt}(n) + l(n)\right),$$

wherein $\Delta \hat{d}(n)$ represents the amount of change in the distance, $\beta(n)$ represents the rotation angle, $l(n)$ represents the displacement, and $\phi_{filt}(n)$ represents the radar signal that is a phase signal or a filtered radar signal.

11. The method of claim 9, wherein
if the radar is the pulse radar, the amount of change in the distance is calculated according to the following equation:

$$\Delta\hat{d}(n) = (1 - \cos\beta(n))(c \cdot p_{filt}(n) + l(n)),$$

wherein $\Delta\hat{d}(n)$ represents the amount of change in the distance, $\beta(n)$ represents the rotation angle, $l(n)$ represents the displacement, $p_{filt}(n)$ represents the radar signal that is a received pulse arrival time or a filtered radar signal, and $c=3\times10^8$ (m/s).

12. The method of claim 4, further comprising,
after obtaining the radar signal,
filtering the radar signal according to a preset band,
wherein the estimating a motion artifact comprises estimating a motion artifact using a filtered radar signal.

13. The method of claim 4, wherein
the target is a human body, and the radar signal is a signal corresponding to heartbeat and respiration of the human body.

14. An apparatus for removing a motion artifact of a radar, comprising:

a filtering unit configured to obtain and filter a radar signal for a target to be measured by the radar;

a radar detection unit configured to measure posture of the radar, wherein the posture of the radar includes a vertical angle at which the radar signal is radiated in a vertical direction about a central axis, a horizontal angle at which the radar signal is radiated in a horizontal direction about the central axis, and displacement of the radar according to movement of the radar; and a radar posture correction unit configured to estimate a motion artifact caused by the movement of the radar based on the vertical angle, the horizontal angle, and the displacement which are provided from the radar detection unit and correct the radar signal provided from the filtering unit according to the motion artifact; wherein the radar posture correction unit is configured to obtain an amount of change in a distance between a surface of the target to be measured and the radar, use the amount of change in the distance as the motion artifact, and correct the radar signal according to the amount of change in distance.

15. The apparatus of claim 14, wherein
the radar posture correction unit is configured to subtract a value corresponding to the amount of change in the distance from the radar signal to obtain a radar signal from which the motion artifact is removed.

16. The apparatus of claim 14, wherein
the radar posture correction unit is configured to calculate the amount of change in the distance based on the radar signal, the vertical angle, and the displacement.

17. The apparatus of claim 14, wherein
the radar posture correction unit is configured to obtain a rotation angle when the radar rotates with the vertical angle and the horizontal angle and calculate the amount of change in the distance based on the radar signal, the rotation angle, and the displacement.

18. The apparatus of claim 14, wherein
the radar signal is a phase signal corresponding to a phase difference between a transmission signal and a reception signal when the radar is a Doppler radar and the radar signal is a received pulse arrival time when the radar is a pulse radar.

19. The apparatus of claim 14, wherein
the radar is unfixed, the target is a human body, and the radar signal is a signal corresponding to a heartbeat and respiration of the human body.

* * * * *